(12) United States Patent
Remde et al.

(10) Patent No.: US 9,205,190 B2
(45) Date of Patent: Dec. 8, 2015

(54) MODULAR INFUSION PUMP

(75) Inventors: Axel Remde, Luetzelflueh (CH); Gilbert Schiltges, Kirchberg (CH)

(73) Assignee: Roche Diagnostics International AG, Steinhausen (CH)

( * ) Notice: Subject to any disclaimer, the term of this patent is extended or adjusted under 35 U.S.C. 154(b) by 1881 days.

(21) Appl. No.: 11/303,738

(22) Filed: Dec. 16, 2005

(65) Prior Publication Data

US 2006/0184119 A1    Aug. 17, 2006

Related U.S. Application Data

(63) Continuation of application No. PCT/EP2004/006482, filed on Jun. 16, 2004.

(30) Foreign Application Priority Data

Jun. 17, 2003  (DE) .................................. 103 27 254

(51) Int. Cl.
*A61M 37/00*     (2006.01)
*A61M 5/145*     (2006.01)
*A61M 5/14*      (2006.01)
*A61M 5/142*     (2006.01)

(52) U.S. Cl.
CPC ......... *A61M 5/14566* (2013.01); *A61M 5/1413* (2013.01); *A61M 5/14244* (2013.01); *A61M 5/14248* (2013.01); *A61M 2205/15* (2013.01); *A61M 2205/18* (2013.01); *A61M 2205/3331* (2013.01); *A61M 2205/3365* (2013.01); *A61M 2205/8212* (2013.01)

(58) Field of Classification Search
CPC ................ A61M 5/14248; A61M 2005/14268
USPC ..................... 604/156, 65–19, 140, 500, 131, 604/890.1–891.1
See application file for complete search history.

(56) References Cited

U.S. PATENT DOCUMENTS

| | | | | |
|---|---|---|---|---|
| 4,140,117 | A * | 2/1979 | Buckles et al. | 604/132 |
| 4,886,499 | A * | 12/1989 | Cirelli et al. | 604/131 |
| 5,062,834 | A | 11/1991 | Gross et al. | |
| 5,984,894 | A | 11/1999 | Poulsen et al. | |
| 6,074,369 | A | 6/2000 | Sage et al. | |
| 6,165,155 | A * | 12/2000 | Jacobsen et al. | 604/156 |
| 6,200,293 | B1 | 3/2001 | Kriesel et al. | |
| 2002/0072733 | A1 | 6/2002 | Flaherty | |
| 2002/0169439 | A1 * | 11/2002 | Flaherty | 604/891.1 |
| 2003/0073952 | A1 | 4/2003 | Flaherty et al. | |
| 2003/0088238 | A1 * | 5/2003 | Poulsen et al. | 604/890.1 |

FOREIGN PATENT DOCUMENTS

| | | |
|---|---|---|
| DE | 198 40 965 A1 | 3/2000 |
| DE | 19840965 A1 | 3/2000 |
| EP | 1 177 802 | 7/2001 |

(Continued)

*Primary Examiner* — Kevin C Sirmons
*Assistant Examiner* — Phillip Gray
(74) *Attorney, Agent, or Firm* — Dinsmore & Shohl LLP

(57) ABSTRACT

A modular infusion pump for administering a product, including a pump housing, a reservoir to contain the product, a delivery device associated with the pump housing to deliver the product from the reservoir, an energy source for the delivery device, another housing separate from the pump housing for receiving the energy source, and a transmission for transmitting energy from the energy source to the delivery device.

23 Claims, 2 Drawing Sheets

(56) References Cited

FOREIGN PATENT DOCUMENTS

| WO | WO 01/70307 | 9/2001 |
| WO | 2002068015 A2 | 9/2002 |
| WO | WO 02/068015 A2 | 9/2002 |
| WO | 2003105930 A2 | 12/2003 |
| WO | WO 03/105930 A2 | 12/2003 |

\* cited by examiner

MODULAR INFUSION PUMP

CROSS-REFERENCE TO RELATED APPLICATION(S)

This application is a continuation of International Application No. PCT/EP2004/006482, filed on Jun. 16, 2004, which claims priority to German Application No. DE 103 27 254.2, filed on Jun. 17, 2003, the contents of both applications are incorporated in their entirety herein.

BACKGROUND

The invention relates to medical devices and methods of making and using them. More particularly, it relates devices for delivering, administering or dosing a substance, including infusion pumps, particularly a modular infusion pump for administering a product such as insulin or another medicament.

Particularly in self-administration of medicaments, for example insulin, the persons using the medicament in question and administering it themselves by means of an infusion pump are increasingly placing importance on convenience and discretion. Manufacturers are meeting these demands by, among other things, dividing the infusion pump into structural assemblies which are each arranged in their own housing and can be joined to one another by wireless or wired connection.

Modular infusion pumps of this kind are known, for example, from DE 30 35 670 A1 and DE 198 40 965 A1. According to these, an infusion pump is split up into a pump head, which is implanted directly on the body or even within the body and comprises a product-containing reservoir and a delivery device, and an operating and control part which can be carried at a distance from the pump head, for example on or in clothing. The operating and control part and the pump head are in wireless communication with one another.

SUMMARY

It is an object of the present invention to further improve the convenience of modular infusion pumps of the type mentioned above.

In one embodiment, the present invention comprises a modular infusion pump for administering a product, including a pump housing, a reservoir to contain the product, a delivery device or mechanism associated with the pump housing to move the product from the reservoir, an energy source for the delivery device, another housing separate from the pump housing for containing the energy source, and means for transmitting energy from the energy source to the delivery device.

In one embodiment, the present invention comprises a modular infusion pump for administering a product, comprising a pump housing, a reservoir for the product, a delivery device, and an energy source. The pump housing is designed such that it can be placed with an underside directly onto human or animal skin. The reservoir can be formed directly by the pump housing or it can comprises a receptacle, in particular an ampoule or vial, exchangeably or replaceably received by the pump housing. The pump housing also stores, contains or houses the delivery device, which comprises a motor for generating a delivery movement. The pump housing forms, together with the infusion pump components received by it, a first module, which may be referred to as a pump head. In one embodiment, the components received by the pump housing are accommodated substantially within the pump housing. However, within the meaning of the invention, received is also understood to refer to those components which may be secured on the outside of the pump housing or are at least not completely enclosed by the pump housing. Nevertheless, complete enclosure and, in this sense, accommodation within the pump housing is one preferred way of arranging, housing and storing the components of the pump head, provided such components do not have to be removed from the pump housing.

For the modular arrangement, the infusion pump comprises a further housing which, in particular, can receive a control device for the delivery device, preferably for a motor of the delivery device, and/or an operating device, and/or a display device for the display of, for example, operational or functional parameters or states of the infusion pump.

According to the invention, however, the further housing in this case receives the energy source for the delivery device. The energy required for operating the delivery device is transmitted by wire between the further housing and the pump housing. Instead of this, however, wireless transmission would also be possible, especially over short distances of approximately 50 cm or less. Other suitable transmission systems or methods may be used as well.

Compared to conventional infusion pumps which combine all pump components in a single housing, the modular infusion pump according to the invention affords the advantage that the reservoir and the delivery device are at all times arranged in immediate proximity to the site of administration, generally a puncture site, and can remain there at least until the reservoir is exchanged, filled or topped up. Compared to known modular infusion pumps, the weight and size of the pump head is reduced. The reduction in the weight and volume of the energy source is not the only advantage of the present invention. By removing the energy source from the pump head, the pump housing can be simplified and the weight and volume of the pump housing itself can also be reduced.

In some preferred embodiments, parts of the control device of the infusion pump, or the whole control device, can be relocated from the pump head. The control device or the relocated parts can be received by the further housing. The control device is divided into a power section, via which the energy source supplies the delivery device with energy, and a signal-processing part which controls the power section and, via the power section, also the delivery device. The control device is developed as a controlling and regulating device, but for the sake of simplicity it may be referred to as a control device. Of the control device, at least either the power section or the signal-processing part, or, in some embodiments preferably both the power section and the signal-processing part, are relocated from the pump housing, i.e., from the pump head.

Of the energy supply system for the delivery device, only the line or the several lines for energy transmission are arranged in the pump housing. The delivery device is also controlled and advantageously regulated via this line or these several lines.

If, as in some preferred embodiments, the control device also regulates the delivery device and accordingly comprises a position and/or speed sensor which detects a position and/or speed of a component of the delivery device, for example preferably of said motor, the pump housing then receives, in addition to the sensor, the lines necessary for the energy supply and/or signal transmission of the sensor, if appropriate only a single line for the combined transmission of energy and signals.

If, as in some preferred embodiments, an occlusion and/or leak detector is to be arranged in the pump housing, then the comments made above concerning the position or speed sensor also apply to the energy supply and signal transmission of this detector.

In one preferred embodiment, the pump housing serves as a support for the reservoir, for components located downstream of the reservoir in a product-carrying system comprising the reservoir, for a drive mechanism generating the delivery movement of the delivery device, and for the other components of the delivery device driven by the drive mechanism. If appropriate, the pump housing is also the support for one or more sensors for controlling the drive mechanism, if the latter is regulated, and for additional monitoring devices, for example an occlusion and/or leak monitor device. Data and/or signals from any sensor associated with the present invention may be processed "on-board" for example, by a controller or processor carried by the medical device, or may be suitably transmitted or communicated, in whole or in part, to a separate controller or processor.

The drive mechanism can be a motor, preferably an electric rotary motor. However, an electric linear motor could also be used. It is, in principle, also quite conceivable for the motor to be a pneumatic or hydraulic motor. The driving of the delivery device can alternatively also be based on other effects, for example a piezo effect. Microsystem pumps are also conceivable. Conventional drives may be preferred, however.

The energy source may comprise an electric battery or an electric accumulator. Here too, however, alternatives are conceivable, for example the energy source being in the form of a pressure reservoir, a fuel cell, or an additional supply pump for supplying a pneumatic or hydraulic motor with the working fluid.

According to another aspect of the invention, an infusion cannula protrudes beyond the underside of the pump housing by a cannula length that is to be introduced into or beneath the skin. This feature is also considered satisfied when, for example, the infusion cannula is guided laterally out of the pump housing and is guided along a side wall of the pump housing to the area of the underside and is then continued past the underside by said cannula length. In one preferred embodiment, the infusion cannula protrudes from the housing only by said cannula length. A connecting line, which connects the reservoir to the infusion cannula, is preferably 5 cm long and, still more preferably, shorter than 5 cm, even without relocation of the energy source from the pump housing. In some embodiments, the cannula protrudes or extends beyond the underside of the pump housing only by a cannula length to be introduced into or beneath the skin.

Since the infusion cannula to be introduced into body tissue is provided directly at or on the pump housing, this ensures that the reservoir and an infusion cannula outlet located in the body tissue have the same hydrostatic height or, at any rate, a difference in height that is negligible for practical purposes. Therefore, a siphoning effect, i.e., a suction situation in the reservoir, resulting in uncontrolled dispensing of product, cannot arise. An advantage is also that product losses associated with a priming of the infusion pump are minimized. Priming is the term used to describe the procedure by which air is removed from the product system extending from the reservoir to the outlet of the infusion cannula. The shortening of the product system also contributes to reducing the risk of occlusions and/or leaks in the system. Also, by omitting a catheter which is guided out from the housing and which in conventional infusion pumps extends as far as the infusion cannula, the number of disposable articles to be kept in stock by the user and to be carried around when traveling can also be reduced.

The reservoir can form a product outlet on the underside of the pump housing, such that the infusion cannula can be directly joined to the reservoir outlet. In the case of the one preferred embodiment, wherein delivery of the product is by means of a piston which is received in the reservoir and can be moved toward a reservoir outlet, the reservoir outlet will in most cases point in the direction of movement of the piston, and therefore in most cases at an angle, in general at a right angle, to the underside of the pump housing. In a preferred embodiment of this type, the connecting line also bridges the angle between the reservoir outlet and the infusion cannula.

In a preferred embodiment, the pump housing is in several parts, e.g., in two parts, and comprises a main housing, which receives or itself forms the reservoir, and a secondary housing from which the infusion cannula protrudes and which is secured on the main housing. The secondary housing is advantageously secured releasably onto the main housing by hand and without aids. After it has been undone, the connection can be re-established by one or more simple maneuvers. The main housing and the secondary housing are connected to one another by means of a suitable coupling, for example in the form of a screw connection, a bayonet connection, a simple plug-in connection, a catch connection or a combined plug-in and catch connection. The main housing and the secondary housing can additionally be locked together when the coupling is designed as a screw or bayonet connection.

The secondary housing forms an angle adapter which bridges an angle between the reservoir outlet and the infusion cannula.

The secondary housing can be connected to the main housing so as to be movable in rotation about at least one axis of rotation, in order to decouple the infusion cannula from rotation movements of the main housing about the axis of rotation. The securing to the main housing can also be so configured that the main housing can execute rotation movements about two or even three axes of rotation relative to the secondary housing, so that still more extensive decoupling is achieved. It is also conceivable that the secondary housing is guided such that it can move in translation on the main housing by a short distance. In one preferred embodiment, the secondary housing is secured rigidly on the main housing, preferably by means of the releasable coupling.

DETAILED DESCRIPTION OF THE DRAWINGS

With regard to fastening, mounting, attaching or connecting the components of embodiments of the present invention, unless specifically described as otherwise, conventional fasteners such as screws, rivets, toggles, pins and the like may be used. Other fastening or attachment means appropriate for connecting components include friction fitting, adhesives, welding and soldering, the latter particularly with regard to electrical or processing components or systems. Any suitable electronic, electrical, communication, control or controller, computer or processing components may be used, including any suitable electrical components and circuitry, wires, wireless components, sensors, chips, boards, micro-processing or control system components, software, firmware, hardware, etc.

Figure 1:
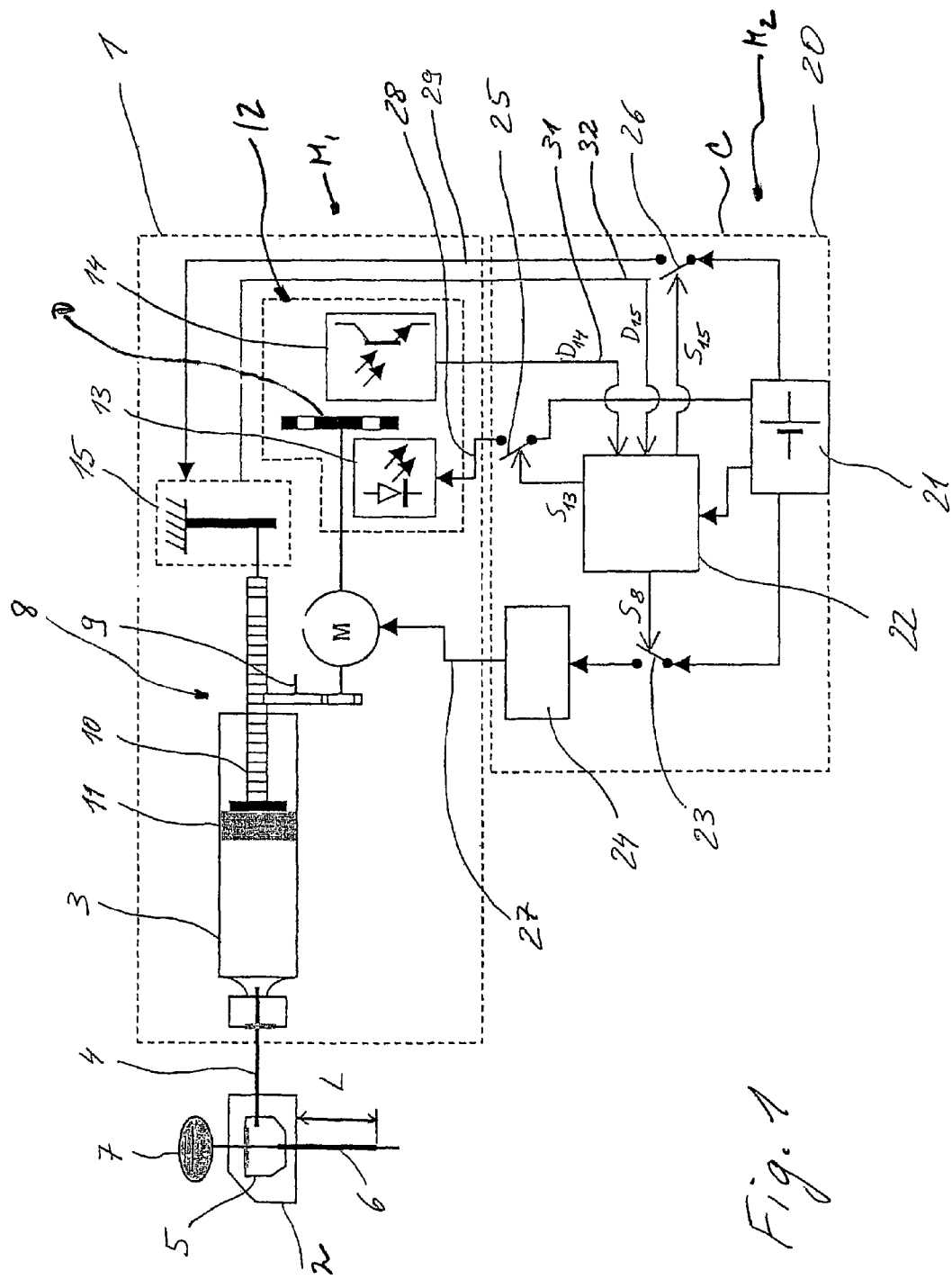
FIG. 1 shows a modular infusion pump according to one embodiment of the present invention.

FIG. 1 shows an infusion pump made up of two modules M1 and M2. A first of the two modules M1 is arranged directly on the skin at an infusion site and may be referred to as the pump head. The pump head comprises a two-part pump housing which lies with an underside on the skin and, for such an arrangement, is equipped with a suitable corresponding securing means, for example an adhesive pad or a strap. The pump head M1 consists of a main housing 1 and a secondary housing 2 which are connected to one another mechanically by means of a coupling mechanism so that they can be easily and quickly released from one another by hand and without aids and can then be connected to one another again.

The main housing 1 accommodates a reservoir 3, which is filled with a liquid product, a delivery device 8 for delivering the product, a position sensor 12 assigned to the delivery device 8, and also an occlusion and leak detector 15. The liquid product can be a liquid medicament in particular, for example insulin. In some embodiments, the delivery device or mechanism 8 is formed conventionally as a piston pump with spindle drive. The force required for delivering the product is generated by means of an electric motor M whose drive speed, translated by a toothed gear wheel 9, is transmitted to a piston rod 10 guided rectilinearly in the axial direction in the main housing 1. The piston rod 10 is formed as a threaded rod. An output gear wheel of the gear 9 is in threaded engagement with the thread of the piston rod 10. Because it is guided rectilinearly, the piston rod 10 is thus moved axially in an advancing direction when the output gear wheel of the gear 9 is driven in rotation. The piston rod 10 then presses against a piston 11 which is received in the reservoir 3 and which is thus moved in the reservoir 3 in the direction toward an outlet of the reservoir 3, the direction of mobility of the piston 11 being identical to the advancing direction of the piston rod 10. An advance movement of the piston rod 10 causes a similar advance movement of the piston 11 and, consequently, the displacement of product through the outlet of the reservoir 3. The delivery device 8 thus accommodates the motor M and all the components arranged downstream in the force flow starting from the motor, including the delivery member acting directly on the product, namely the piston 11.

The product is administered through a flexible infusion cannula 6. The infusion cannula 6 protrudes or extends from the underside of the secondary housing 2; in the illustrative embodiment it protrudes through a housing wall forming the underside of the secondary housing 2. For subcutaneous administration, the infusion cannula 6 is introduced into the body tissue by its entire cannula length L protruding beyond the underside of the secondary housing 2. The cannula length L is the length of the infusion cannula 6 measured between the underside of the secondary housing 2 and the front free end of the infusion cannula 6.

Besides the product-carrying parts extending from the reservoir 3 to the infusion cannula 6, the motor M, the components of the delivery device 8 arranged downstream of the motor M, and the sensors 13, 14 and 15, the pump head only comprises lines for supply of energy to these components and for signal transmission to and from these components. All other components of the infusion pump are integrated in another module $M_2$ with a separate, second housing 20. The further module is a service module in which, in particular, the energy supply for all the components of the pump head is integrated or contained. It also integrates all the functions for control and regulation of the components of the pump head. Where, because of the feedback of one or more variables, the system is not only controlled but also regulated, the following will deal, for the sake of simplicity, only with the control and, accordingly, with a control device or, in brief, a control (the control may take the form or or comprises a suitable processing device, e.g., a microprocessor, etc.) In addition to the two functions of energy supply and control, the service module $M_2$ also integrates the operating functions and optical and/or acoustic display functions. The pump head therefore contains those components of the infusion pump which are needed for delivering the product and for monitoring correct delivery, and it therefore has a low weight and a small volume. By virtue of these two properties, the pump head is well-suited for arrangement directly at the infusion site. Because of the arrangement directly on the body, however, the pump housing can advantageously receive a vibration alarm.

The housing 20 of the service module accommodates an energy source 21 which supplies the required energy to all the components of the infusion pump. In the illustrative embodiment, the energy source 21 is a battery or an electric accumulator. A control device is also shown, with its main inputs and outputs. The control device comprises a signal-processing part 22 and, especially for the motor M, a power section 24, in the illustrative embodiment power electronics. It also comprises several interrupters, namely an interrupter 23 in the energy supply line for the motor M, an interrupter 25 in the energy supply line for the position sensors, and an interrupter 26 in the energy supply line for the occlusion and leak detector 15. All three energy supply lines issue from the common energy source 21. Of course, the energy source 21 can also be formed by a number of separate energy sources in combination. However, the energy source 21 may be constituted in its entirety by a single battery or a single accumulator. The signal-processing part 22 controls each of the interrupters 23, 25 and 26 by means of the latter's own actuating signal, namely by means of an actuating signal S8 for the interrupter 23, an actuating signal $S_{13}$ for the interrupter 25, and an actuating signal $S_{15}$ for the interrupter 26. The output signals of the sensors or detectors are fed to the input of the signal-processing part 22. The output signal of the position sensors 12 is designated by $D_{14}$, and the output signal of the occlusion and leak detector 15 is designated by $D_{15}$.

The output signal $D_{14}$ represents the rotation angle position of the motor M. For detection of the rotation angle position, the position sensor 12 comprises a perforated disk D which is mounted, fixed in terms of rotation, on a shaft of the motor M. A light-emitting diode 13 is arranged to one axial side of the perforated disk D, and a phototransistor 14 to the other side, both of these secured to the housing. The phototransistor 14 receives the light emanating from the light-emitting diode 13, and passing through the perforated disk D, and emits it as output signal $D_{14}$ to the input of the signal-processing part 22 via a signal line 31. The output signal $D_{14}$ of the position sensor 12 forms the controlled variable for controlling the motor M. The signal-processing part 22 generates the reference variable in accordance with a predetermined program, compares this with the controlled variable $D_{14}$ and, as a function of this comparison, forms the actuating signal $S_8$ for the interrupter 23. Depending on the actuating signal $S_8$, the interrupter 23 adopts one of two possible switch positions. In one switch position, it closes the line for energy supply to the motor M, and, in the other case, it interrupts this line. The motor control can be of a conventional nature and therefore does not require any further explanation here, other than to point out that all its components, except for the line 27 for energy supply to the motor M, are components of the service module $M_2$ and not of the pump head. Because of the slip-free transmission of force from the motor M to the piston rod 10, the rotation angle position of the motor M at the same time also represents the position of the piston rod 10 and, consequently, of the piston 11 in the reservoir 3. From the rotation angle position of the motor M, it is therefore possible to draw conclusions directly concerning the amount of product delivered and the residual amount remaining in the reservoir 3. The position sensor(s) 12 may also be used, in principle, to determine the number of revolutions and thus the speed of rotation of the motor M and, consequently, the advancing speed of the piston 11 and thus the delivery speed or delivery rate.

The interrupter 25, arranged for energy-saving reasons in the energy supply line for the light-emitting diode 13, is likewise a simple switch with two positions which closes the energy supply line in one of the two positions and interrupts it in the other position. The interrupter 25 is also a component of the service module and is arranged in the housing 20 of the latter. Only the remaining part 28 of the energy supply line for the light-emitting diode 13 and the remaining part of the signal line 31 are accommodated in the main housing 1 of the pump head.

The occlusion and leak detector is used to measure the reaction force acting on the piston rod 10 during delivery, and the output signal $D_{15}$ represents the measured reaction force. The occlusion and leak detector 15 serves exclusively for monitoring purposes. If, on the basis of the output signal $D_{15}$, the signal-processing part 22 determines the occurrence of an occlusion or a leak in the product-carrying part of the infusion pump, the signal-processing part 22 interrupts the energy supply to the motor M by means of a corresponding actuating signal $S_8$ and thus stops the delivery device 8.

The position sensor(s) 12 can, of course, also serve as a further monitoring device. For example, as a function of its output signal $D_{14}$, a vibratory alarm signal could be emitted by means of a vibration alarm.

In the illustrative embodiment, the occlusion and leak detector 15 is also supplied with energy, namely via its own energy supply line 29 from the energy source 21. The interrupter 26, also formed as a single switch with two possible positions, is arranged in the energy supply line. As regards the energy supply for the detector 15 and the latter's output signal, once again only the remaining parts of the lines 29 and 32 are arranged in the pump housing, so as to minimize the volume and weight of the pump head.

The two interrupters 25 and 26 serve to save energy and assume their respective closed position during running of the motor. They are preferably brought directly into the closed position when the control C is switched on, and they are brought immediately from the closed position to the interrupt position each time this is switched off. If the occlusion and leak detector 15 is configured as a force sensor, it can be formed, for example, as a strain gauge or instead, for example, as a piezoelectric transducer and thus work without energy supply. If the occlusion and leak detector works without external energy, it is thus advantageously possible to dispense with the energy supply line 29 provided for it and with the interrupter 26 and the signal line or signal emitter for the actuating signal $S_{15}$.

If the pump head has a vibration alarm, as is preferred, such a vibration alarm would, for example like the position sensor 12, be supplied with electrical energy from the energy source 21. A further interrupter in the nature of the interrupters would be arranged in the supply line and would be controlled from the signal-processing part 22 by a corresponding actuating signal in such a way that the energy supply line to the vibration alarm would be closed and the vibratory alarm signal triggered. Because the pump head is applied directly on the skin, a vibratory alarm is particularly effective.

Another particularly advantageous feature of the pump head is the short length of the product line to the infusion cannula 6, this length being measured between the outlet of the reservoir 3 and the upstream end of a cannula length L. The cannula length L is the length by which the infusion cannula 6 protrudes into the body tissue during administration of the medicament. When the cannula length L is introduced into the body tissue, the product line length is the length measured between the outlet of the reservoir 3 and the surface of the skin. This length is not more than 5 cm, preferably not more than 2 cm, and it can be less still.

The product line is formed by a connecting cannula 4, a cavity enclosed by a diaphragm 5, and an upstream endpiece of the infusion cannula 6 with which the infusion cannula 6 protrudes into the secondary housing 2. The connecting cannula 4 penetrates a septum which closes the outlet of the reservoir 3. At its opposite downstream end, the connecting cannula 4 penetrates a side wall of the diaphragm 5 and protrudes there into the cavity of the diaphragm 5. Downstream from the connecting cannula 4, the infusion cannula 6 likewise protrudes with its upstream end into the cavity, so that a liquid-tight product line is created from the outlet of the reservoir 3 into the infusion cannula 6.

Since the infusion cannula 6 in the illustrative embodiment is flexible and, in particular, not resistant to bending, it is introduced with the aid of a puncture needle 7 into the body tissue, i.e., into the skin or preferably through the skin. The puncture needle 7 has a sufficient stiffness to allow puncturing. The infusion cannula 6 bears tightly around the puncture needle 7 so that, as the puncture needle 7 punctures the skin, it is introduced along with the puncture needle 7 into the body tissue. After the infusion cannula 6 has been introduced, the puncture needle 7 is withdrawn from the body tissue and from the infusion cannula 6 and from the diaphragm 5. After withdrawal of the puncture needle 7, the diaphragm 5 still seals the hollow cavity joining the connecting cannula 4 and the infusion cannula 6.

For introducing the infusion cannula 6 into the body tissue, it is advantageous if, as in the illustrative embodiment, the secondary housing 2 is connected to the main housing 1 of the pump head in such a way that, when it is placed on the skin, the infusion cannula 6 is also simultaneously introduced into the skin or through the skin and into the body tissue, and no additional maneuver is needed for this other than that of placement of the pump housing. In one preferred and simple configuration, the secondary housing 2, as in the illustrative embodiment, is connected to the main housing 1 in a substantially completely rigid, i.e., immovable, manner, for example by means of a suitable structure such as a bayonet catch or another suitable catch acting as a coupling. The main housing 1 and the secondary housing 2 preferably form a common smooth underside for placement on the skin. The secondary housing 2 moreover forms an adapter which bridges the angle between the outlet of the reservoir 3 and the surface of the skin.

Figure 3:
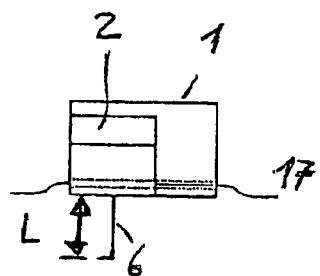
FIG. 3 shows the pump head in a front view.
Figure 2:
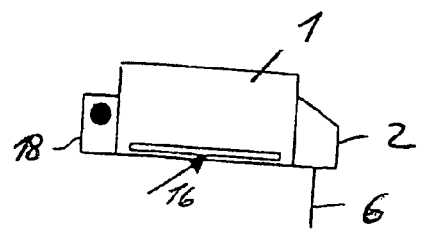
FIG. 2 shows a pump head of the infusion pump in a side view.
Figure 4:
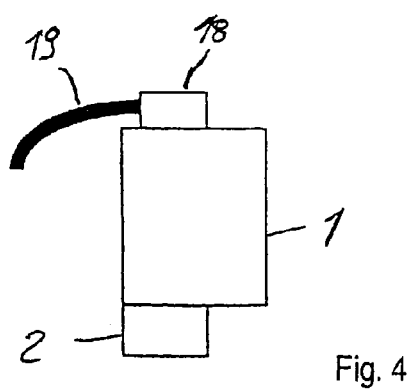
FIG. 4 shows the pump head in a plan view.

FIGS. 2, 3 and 4 show the pump head in different views of the pump housing. The infusion cannula 6 has been introduced by its cannula length L into the body tissue. For placing the pump housing on the skin, FIG. 2 shows a slit formed close to the underside of the pump housing for a securing means 17, for example an adhesive pad or a fastening strap. FIG. 3 shows, in a front view of the side face of the secondary housing 2, an adhesive pad which is pulled through the slit 16 and which protrudes from the main housing 1 through both sides of the slit 16 and can be affixed with its two free ends on the surface of the skin. The infusion cannula 6 is perpendicular with respect to the underside (plane in the illustrative embodiment) of the pump housing sitting on the skin at the infusion site.

FIGS. 2 and 4 also show a plug-in connector 18 which is inserted into a socket of the main housing 1. All the energy and all the signals are transmitted to and from the pump head via the plug-in connector 18 and via the connecting cable 19 issuing from it. In the illustrative embodiment, the transmission takes place exclusively between the pump head and the service module. The plug-in connector 18 is designed as an angled plug-in connector. The connecting cable 19 leaves the plug-in connector 18 at a right angle to the attachment to the pump head. Although a straight axial attachment is also possible in principle, the design as an angled plug-in connector is preferred because, in this way, the transverse forces acting on the infusion cannula 6 during movements of the body can be reduced. The plug-in connector 18 is water-tight. The connecting cable 19 is a highly flexible and shielded electrical line. The connecting line 19 is either an integral component of the control C or is coupled to this control C likewise via a plug-in connector and a corresponding attachment on the housing 20.

The integrity and correct function of an infusion pump in accordance with the present invention can be monitored, on the basis of the energy supply and signal connection, more easily than in conventional infusion pumps where a long connecting catheter extends from the infusion pump all the way to the infusion site. In one embodiments, monitoring can be accomplished by measuring the impedance, this impedance measurement being carried out permanently or at regular intervals. By monitoring the energy supply and signal connections, it is possible to detect and to differentiate between relevant error situations, for example an interruption or a short circuit, caused for example by penetration of moisture. Compared to known pump heads which are also placed directly in the skin, at least one advantage is the shortened product line between the outlet of the reservoir 3 and the cannula length L by which the infusion cannula 6 is introduced into the body tissue.

Another inherent advantage of the pump head that may be mentioned is the possibility that, on the one hand, a flow sensor can be arranged in immediate proximity to the cannula length L introduced into the body tissue and that, on the other hand, the connection needed for signalling and, if necessary, for the energy supply of the flow sensor can be made not via flexible line catheters, but instead via the pump housing which, although of more than one part, constitutes a uniform pump housing in the assembled state. This is not only advantageous in the case of a wired connection, but also in the case of a wireless connection of the flow sensor. The connection and integration of a flow sensor into the control system C would, for example, be like the connection and integration of the occlusion and leak detector 15.

The secondary housing 2, with all the pump head components received by it, is designed as a disposable article. This disposable article can, for example, be exchanged each time the reservoir is filled, refilled, topped up or completely replaced. The life time of the disposable article can, however, also be longer. The disposable article includes the components accommodated in the secondary housing 2 and of course also the infusion cannula 6 and preferably also the connecting cannula 4. When the secondary housing 2 is secured on the main housing 1, the connection to the reservoir 3 is also established at the same time.

In the foregoing description, embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A modular infusion pump for administering a product, said infusion pump comprising:
 a) a pump housing comprising a main housing and a secondary housing releasably secured to the main housing by a coupling, the secondary housing comprising an underside for contacting human or animal skin and defines a cavity of a diaphragm that is separate from the main housing,
 b) a reservoir to contain the product, said reservoir received in or formed by the main housing,
 c) a delivery device housed in the pump housing for delivering the product from the reservoir,
 d) an energy source for the delivery device,
 e) a further housing separate from the pump housing, said further housing receiving the energy source, and
 f) a transmission device for transmitting energy from the energy source to the delivery device; and
 g) the cavity joining a connecting cannula and an infusion cannula that are physically separate, the connecting cannula that penetrates a septum which closes an outlet of the reservoir, and at an opposite downstream end of the connecting cannula, the connecting cannula penetrates a side wall of the diaphragm and protrudes into the cavity of the diaphragm;
 h) a puncture needle placeable entirely through the diaphragm; and
 i) the infusion cannula upstream end protrudes into the cavity, the infusion cannula bearing around the puncture needle so that, as the puncture needle punctures the skin, it is introduced along with the puncture needle into the body tissue, and after the infusion cannula has been introduced, the puncture needle is withdrawn from the body tissue and from the infusion cannula and from the diaphragm, and after withdrawal of the puncture needle, the diaphragm still seals the cavity joining the connecting cannula and the infusion cannula.

2. The modular infusion pump as claimed in claim 1, wherein the infusion pump comprises a control device with a power section via which the energy source supplies the delivery device with energy, the power section contained the further housing.

3. The modular infusion pump as claimed in claim 1, wherein the infusion pump comprises a control device with an interrupter in order to interrupt the energy supply to the delivery device in a controlled manner, the interrupter contained in the further housing.

4. The modular infusion pump as claimed in claim 1, further comprising a detector arranged in or on the pump housing for detecting a physical parameter of the delivery device or of a product-carrying part, said detector sending to a control device of the infusion pump an output signal ($D_{14}$, $D_{15}$)

representing the detected parameter, as a function of which the control device provides an actuating signal ($S_8$) for the delivery device.

5. The modular infusion pump as claimed in claim 4, wherein the energy source supplies the detector with energy via an interrupter which the control device controls by means of an actuating signal ($S_{13}$, $S_{15}$).

6. The modular infusion pump as claimed in claim 5, wherein the interrupter is arranged in the further housing.

7. The modular infusion pump as claimed in claim 4, wherein the detector is one of a position sensor or speed sensor which detects, respectively, a position or a speed of the delivery device, the output signal ($D_{14}$) of the detector representing the detected position or speed.

8. The modular infusion pump as claimed in claim 4, wherein the detector is at least one of an occlusion and leak detector which detects, respectively, an occlusion or a leak in a product-carrying part of the infusion pump extending from the reservoir as far as an outlet of an infusion cannula.

9. The modular infusion pump as claimed in claim 4, wherein the detector is a flow detector arranged in line with an infusion cannula in a product-carrying part of the infusion pump.

10. The modular infusion pump as claimed in claim 1, further comprising an energy supply system comprising the energy source and a means for energy transmission in or on the pump housing.

11. The modular infusion pump as claimed in claim 1, further comprising an energy supply system for the infusion pump, said energy supply system comprising the energy source and a means for energy transmission in or on the pump housing.

12. The modular infusion pump as claimed in claim 1, further comprising a control and energy supply system for the delivery device, said control and energy supply system comprising the energy source, a control device and means for energy transmission and signal transmission in or on the pump housing.

13. The modular infusion pump as claimed in claim 1, wherein the delivery device comprises a motor and at least one delivery member driven by the motor to deliver the product, the energy source supplying the motor with required energy.

14. The modular infusion pump as claimed in claim 1, wherein the pump housing and the further housing are connected to one another by means of at least one energy supply line.

15. The modular infusion pump as claimed in claim 14, wherein the energy supply line comprises a wire and the entire energy transmission between the pump housing and the further housing is via the wire.

16. The modular infusion pump as claimed in claim 1, wherein the pump housing and the further housing are connected to one another by means of at least one signal line.

17. The modular infusion pump as claimed in claim 16, wherein the at least one signal line comprises at least one wire and the entire signal transmission between the pump housing and the further housing is via the at least one wire.

18. The modular infusion pump as claimed in claim 1, wherein the infusion cannula protrudes from the underside of the secondary housing only by the cannula length to be introduced into or through the skin.

19. The modular infusion pump as claimed in claim 1, wherein the reservoir and the infusion cannula are connected by an angle adapter arranged in or on the secondary housing.

20. The modular infusion pump as claimed in claim 1, wherein the secondary housing is moveably and guidedly secured to the main housing.

21. A modular infusion pump for administering a product, said infusion pump comprising:
   a) a pump housing comprising a main housing and a secondary housing releasably secured to the main housing by a mechanical coupling, the secondary housing defines a cavity of a diaphragm that is separate from the main housing, and the main housing and the secondary housing forming a common substantially smooth underside for contacting human or animal skin,
   b) a reservoir to contain the product, said reservoir received in or formed by the main housing,
   c) a delivery device housed in the main housing for delivering the product from the reservoir,
   d) an energy source for the delivery device,
   e) a further housing separate from the pump housing, said further housing receiving the energy source,
   f) a transmission device for transmitting energy from the energy source to the delivery device; and
   g) the cavity joining a connecting cannula and an infusion cannula that are physically separate, the connecting cannula that penetrates a septum which closes an outlet of the reservoir, and at an opposite downstream end of the connecting cannula, the connecting cannula penetrates a side wall of the diaphragm and protrudes into the cavity of the diaphragm;
   h) a puncture needle placeable entirely through the diaphragm; and
   i) the infusion cannula upstream end protrudes into the cavity, the infusion cannula bearing around the puncture needle so that, as the puncture needle punctures the skin, it is introduced along with the puncture needle into the body tissue, and after the infusion cannula has been introduced, the puncture needle is withdrawn from the body tissue and from the infusion cannula and from the diaphragm, and after withdrawal of the puncture needle, the diaphragm still seals the cavity joining the connecting cannula and the infusion cannula.

22. The modular infusion pump as claimed in claim 21, wherein the flexible infusion cannula is coupled to the secondary housing such that the flexible infusion cannula is substantially fixed relative to the secondary housing.

23. The modular infusion pump as claimed in claim 21, wherein the delivery device comprises a motor and at least one delivery member driven by the motor to deliver the product, the energy source supplying the motor with required energy.

* * * * *